US007754502B1

(12) United States Patent
Yegnashankaran

(10) Patent No.: US 7,754,502 B1
(45) Date of Patent: Jul. 13, 2010

(54) BACKSIDE DEFECT DETECTOR AND METHOD THAT DETERMINES WHETHER UNWANTED MATERIALS ARE PRESENT ON THE BACKSIDE OF A SEMICONDUCTOR WAFER

(75) Inventor: Visvamohan Yegnashankaran, Cupertino, CA (US)

(73) Assignee: National Semiconductor Corporation, Santa Clara, CA (US)

( * ) Notice: Subject to any disclaimer, the term of this patent is extended or adjusted under 35 U.S.C. 154(b) by 777 days.

(21) Appl. No.: 11/588,742

(22) Filed: Oct. 27, 2006

(51) Int. Cl.
*H01L 21/66* (2006.01)
*G01N 21/86* (2006.01)

(52) U.S. Cl. ..................... 438/14; 250/559.4

(58) Field of Classification Search ............. None
See application file for complete search history.

(56) References Cited

U.S. PATENT DOCUMENTS

| | | | | |
|---|---|---|---|---|
| 6,107,107 | A * | 8/2000 | Bruce et al. | 438/14 |
| 6,825,487 | B2 * | 11/2004 | Preece | 250/559.4 |
| 7,062,399 | B1 * | 6/2006 | Bruce et al. | 702/117 |
| 2004/0021097 | A1 * | 2/2004 | Preece | 250/559.4 |

OTHER PUBLICATIONS

Alan Carlson and Tuan Le, "Correlation of Wafer Backside Defects to Photolithography Hot Spots Using Advanced Macro Inspection", Presented at 31st International Symposium, Microlithograpy—An SPIE Event, Feb. 2006, pp. 1-7.
Nanomatrics Incorporated—Process Control Metrology Solutions, [online], [retrieved on Jun. 16, 2006]. Retrieved from the Internet: http://www.nanometrics.com/products/tech_extrem_darkfield.html, pp. 1 of 1.
Chandra Saravanan et al., MICRO:Lead News, "Investigating the Impact of Backside Defect Ispection on Process Development and Yields", [online], [retrieved on Jun. 16, 2006]. Retrieved from the Internet: http://www.micromagazine.com/grabber.php3?URL=http://micromagazine.com/arc..., pp. 1-8.
Peter Gise and Ray Hoobler, "Integrated Metrology Adopts Stronger APC Role", Nanometrics Inc., May 1, 2004, [online], [retrieved on Jun. 16, 2006]. Retrieved from the Internet: http://www.reed-electronics.com/semiconductor/index.asp?layout=articlePrint&articleID..., pp. 1-5.
"Results of Ultra-Clean Processing", [online], [retrieved on Jun. 16, 2006]. Retrieved from the Internet: http://www.imec.be/wwwinter/mediacenter/en/SR2005/html/142152.html., pp. 1-11.
Electron Microscopy, "Image Modes in TEM—Dark Field Images", [online], [retrieved on Jun. 16, 2006]. Retrieved from the Internet: http://www.microscopy.ethz.ch/TEM_DF.htm, pp. 1-2.

(Continued)

*Primary Examiner*—Charles D Garber
*Assistant Examiner*—Andre' C Stevenson
(74) *Attorney, Agent, or Firm*—Mark C. Pickering

(57) ABSTRACT

Minute materials which can be undesirably left on the backside of a semiconductor wafer are detected by scanning the semiconductor wafer with an infra-red (IR) light following the completion of a process step that forms and then selectively removes a material from the top surface of the wafer. Any detected material can then be removed from the backside of the wafer to ensure that that backside of the wafer is clean and flat.

20 Claims, 2 Drawing Sheets

OTHER PUBLICATIONS

PatentView/EP1457828, "Software Patent:Focus Spot Monitoring in a Lithographic Projection Apparatus", [online], [retrieved on Jun. 16, 2006], Retrieved from the Internet: http://gauss.ffii.org/PatentView/EP1457828?action=print, pp. 1-20.

* cited by examiner

BACKSIDE DEFECT DETECTOR AND METHOD THAT DETERMINES WHETHER UNWANTED MATERIALS ARE PRESENT ON THE BACKSIDE OF A SEMICONDUCTOR WAFER

BACKGROUND OF THE INVENTION

1. Field of the Invention

The present invention relates to backside defect detectors and, more particularly, to a backside defect detector and method that utilizes an IR light scan to determine whether unwanted materials are present on the backside of a semiconductor wafer.

2. Description of the Related Art

During a conventional semiconductor wafer fabrication process, a number of materials are formed on the surface of a semiconductor wafer, and then selectively removed during a series of steps that form a structure which operates as an electrical circuit. Typically, the materials that are formed on the front side of the wafer are also formed on the backside of the wafer.

One well-known and common fabrication step is photolithography. In photolithography, a photoresist is formed on the top surface of a wafer. The photoresist is then patterned, developed, baked, and partially removed to form a mask that exposes regions of an underlying material. In most cases, the photoresist has an etch rate that is substantially different from the etch rates of the exposed materials that underlie the mask.

After the mask has been formed, the next fabrication step is typically to etch the exposed materials using a wet and/or dry etchant. The etchant removes the materials that are exposed by the mask over a period of time due to the difference in etch rates between the photoresist and the exposed materials.

The backside of the wafer is often exposed so that a wet etchant can be used to remove the materials that were formed on the backside of the wafer. Ideally, the wet etchant removes all of the materials that were formed on the backside of the wafer so that the backside of the wafer is clean and flat.

In actual practice, however, after the etch step has been completed, minute amounts of materials can undesirably remain on the backside of the semiconductor wafer. The minute amounts of material that remain on the backside of the wafer, in turn, can distort the flatness of the backside of the wafer.

As a result, the next time the backside of the wafer is placed on a flat surface for processing, the distorted backside causes the top surface of the wafer to also be distorted. In other words, locations across the top surface of the wafer which are intended to have the same height can have different heights when measured normal to the flat surface.

Thus, when a photoresist is subsequently deposited across the top surface of the wafer, the photoresist does not have a uniform depth in each of the places where the depth should be uniform. The lack of uniform depth leads to focus spots that alter the image pattern that is formed in the photoresist.

As a result, non-uniform opening sizes can be formed when the photoresist is subsequently developed, baked, and removed to form a mask. In sub-micron applications, these non-uniform opening sizes can lead to improperly sized devices that fail to meet specification or fail to operate all together.

Therefore, to reduce the photolithographic distortion (the focus spots) that are due to minute materials that undesirably remain on the backside of the wafer, and the resulting non-uniform opening sizes, there is a need for an apparatus and method that determines whether unwanted materials are present on the backside of a semiconductor wafer following a processing step, and therefore whether the backside of the wafer is clean and flat and ready for a subsequent processing step.

DETAILED DESCRIPTION OF THE INVENTION

Figure 1:
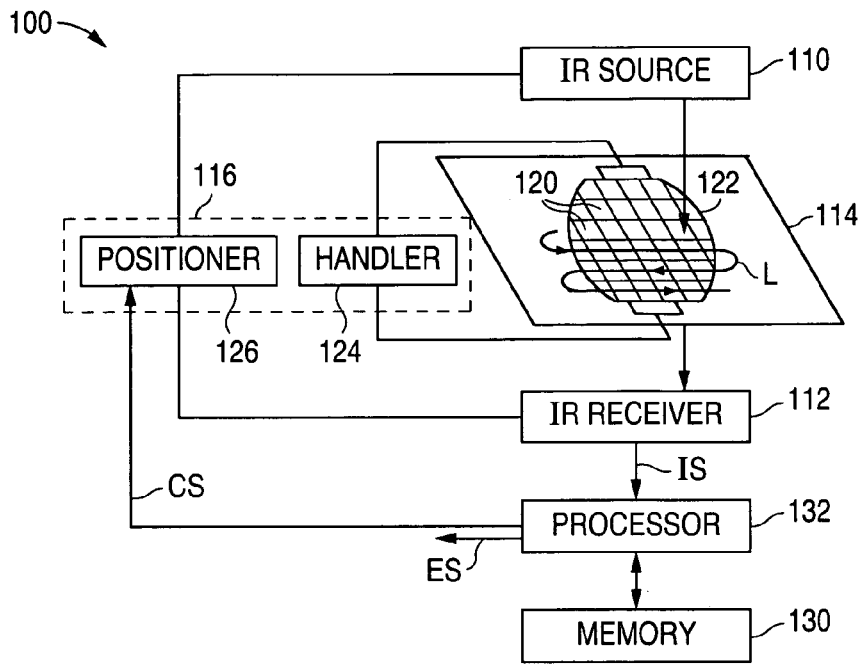
FIG. 1 is a block diagram illustrating an example of a backside defect detector 100 in accordance with the present invention.

FIG. 1 shows a block diagram that illustrates an example of a backside defect detector 100 in accordance with the present invention. As described in greater detail below, backside defect detector 100 detects the presence of minute materials which have been unintentionally left on the backside of a semiconductor wafer, following the completion of a process step that forms and then selectively removes a material from the top surface of the wafer. The detection of minute materials allows the minute materials to be removed from the backside of the wafer, thereby ensuring that the backside of the wafer is clean and flat before proceeding to a subsequent fabrication step.

As shown in FIG. 1, backside defect detector 100 includes an infra-red (IR) source 110 and an IR receiver 112 that lie on opposite sides of a plane 114. IR source 110 outputs one or more wavelengths of IR light. IR receiver 112 detects the one or more wavelengths of IR light, and generates an intensity signal IS that indicates a magnitude of the received IR light.

As further shown in FIG. 1, backside defect detector 100 includes a scanner 116 that scans rows and columns of grid areas 120 on a semiconductor wafer 122 that lies within plane 114 with IR source 110 and IR receiver 112. The scan generates a detected intensity value for each grid area 120 of semiconductor wafer 122.

In the FIG. 1 example, scanner 116 is implemented with a handler 124 that holds semiconductor wafer 122 in a fixed position within plane 114, and a positioner 126 that is connected to IR source 110 and IR receiver 112 to move IR source 110 and IR receiver 112 about plane 114 so that IR source 110 and IR receiver 112 can be placed on opposite sides of each grid area 120 of semiconductor wafer 122. As a result, IR receiver 112 can receive the IR wavelength of light that passes through each grid area 120.

For example, as shown by the serpentine line L in FIG. 1, positioner 126 can be implemented as a raster scanner that continuously moves IR source 110 and IR receiver 112 column-by-column and row-by-row over each grid area 120 of semiconductor wafer 122. Alternately, other types of continuous scan patterns can be used to place IR source 110 and IR receiver 112 on opposite sides of each grid area 120 of semiconductor wafer 122.

In addition, backside defect detector 100 includes a memory 130 and a processor 132. Memory 130 holds a stored intensity value for each grid position 120 for each of a number of separate etch steps. Each stored intensity value, in turn, represents an intensity value of a known good wafer. For example, the intensity values held by memory 130 can be determined by processing a number of known good wafers with backside defect detector 100, and storing, for example, a mean of the detected intensity values.

Processor 132 is connected to IR receiver 112, scanner 116, and memory 130. Processor 132 outputs a control signal CS to scanner 116 to control the movement of positioner 126 and, therefore, the movement of IR source 110 and IR receiver 112 so that IR source 110 and IR receiver 112 can be placed on opposite sides of each grid area 120 of semiconductor wafer 122.

Processor 132 also receives the intensity signal IS from IR receiver 112, and digitizes the intensity signal IS to generate a detected intensity value for each grid area 120. Alternately, IR receiver 112 can digitize the magnitude of the received IR light and output the intensity signal IS as a series of digital values that represent the detected intensity value for each grid area 120. In this case, processor 132 reads the detected intensity value for each grid area 120 from IR receiver 112.

Once the detected intensity value has been determined for a grid area 120, processor 132 compares the detected intensity value to the stored intensity value from memory 130 that corresponds with the grid area 120. When processor 132 determines that the detected intensity value for a grid area 120 does not fall within a predetermined error tolerance of the stored intensity value, processor 132 outputs an error signal ES that indicates that the intensity values for the grid area 120 do not match. Processor 132 can be implemented as logic or as a controller that executes code.

Figure 2:
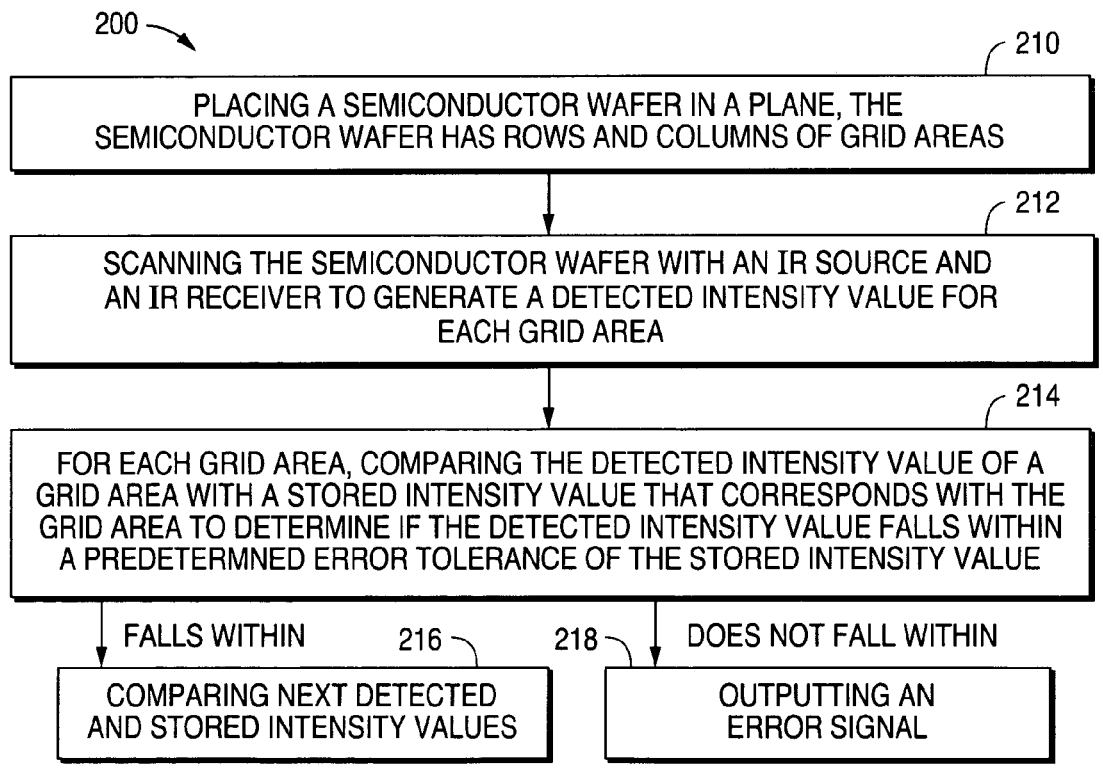
FIG. 2 is a flow chart illustrating an example of a method 200 of operating a backside defect detector in accordance with the present invention.

FIG. 2 shows a flow chart that illustrates an example of a method 200 of operating a backside detector in accordance with the present invention. As shown in FIG. 2, method 200 begins in 210 by placing a semiconductor wafer in plane. The semiconductor wafer has rows and columns of grid areas.

In 212, the semiconductor wafer is scanned with an IR source and an IR detector to generate a detected intensity value for each grid area of the semiconductor wafer. In 214, for each grid area, the detected intensity value of a grid area is compared to a stored intensity value from a memory that corresponds with the grid area to determine if the detected intensity value falls within a predetermined error tolerance of the stored intensity value.

In 216, when the detected intensity value and the stored intensity value for a grid position fall within the predetermined error tolerance, the next detected intensity value and stored intensity value are compared. On the other hand, in 218, when the detected intensity value and the stored intensity value for a grid position do not fall within the predetermined error tolerance, an error signal is output that indicates that the intensity values for the grid position do not match.

For example, a common step that occurs in the beginning of a fabrication process is the formation of isolation trenches, which typically includes the formation and selective removal of an isolation material, such as oxide or nitride, that contacts the top surface of the semiconductor wafer. After the isolation trench formation step has been completed, the semiconductor wafer can be processed according to the present invention.

IR passes through silicon and polysilicon, but not through oxide or nitride. Thus, the scan in 212 produces a pattern that can be compared to a golden pattern from a known good wafer which was previously processed with detector 100, and thereby determine if any minute particles of the isolation material have been left on the backside of the semiconductor wafer.

As a result, the error signal can be used to indicate that further cleaning of the backside of the semiconductor wafer is required to remove all of the minute particles of the isolation material. On the other hand, if no error signal is received by the end of the scan, then all of the minute particles have been successfully removed.

Another common fabrication step is the formation and selective removal of oxide on the top surface of a semiconductor wafer to form a number of gate oxide regions. In the present invention, after the gate oxide formation step has been completed, the semiconductor wafer can be processed according to the present invention.

IR passes through the semiconductor wafer, but not through the isolation material and the gate oxide regions. Thus, the scan in 212 produces a pattern that can be compared to the golden pattern from the known good wafer, and thereby determine if any minute particles of the gate oxide have been left on the backside of the semiconductor wafer.

Up to the formation of the first dielectric layer and the first metal layer of the interconnect structure, the semiconductor wafer can be processed by backside defect detector 100 after the deposition and selective removal of each type of semiconductor material that blocks the passage of IR light through the semiconductor wafer.

Conventionally, prior to forming the first metal layer, the first layer of dielectric material is formed over the top surface of the semiconductor wafer, and then contact openings are formed through the first layer of dielectric material to expose conductive regions, such as source regions, drain regions, and gates. Following this, the first layer of metal is deposited to fill up the contact openings.

Next, the wafer is planarized to remove the first layer of metal from the top surface of the first layer of dielectric material to form contact structures that are electrically connected to the conductive regions. However, after the first layer of dielectric material and the first metal layer have been removed from the backside of the semiconductor wafer, the first layer of dielectric material and the metal contacts formed through the dielectric layer prevent any IR light from passing through the wafer.

Figure 3:
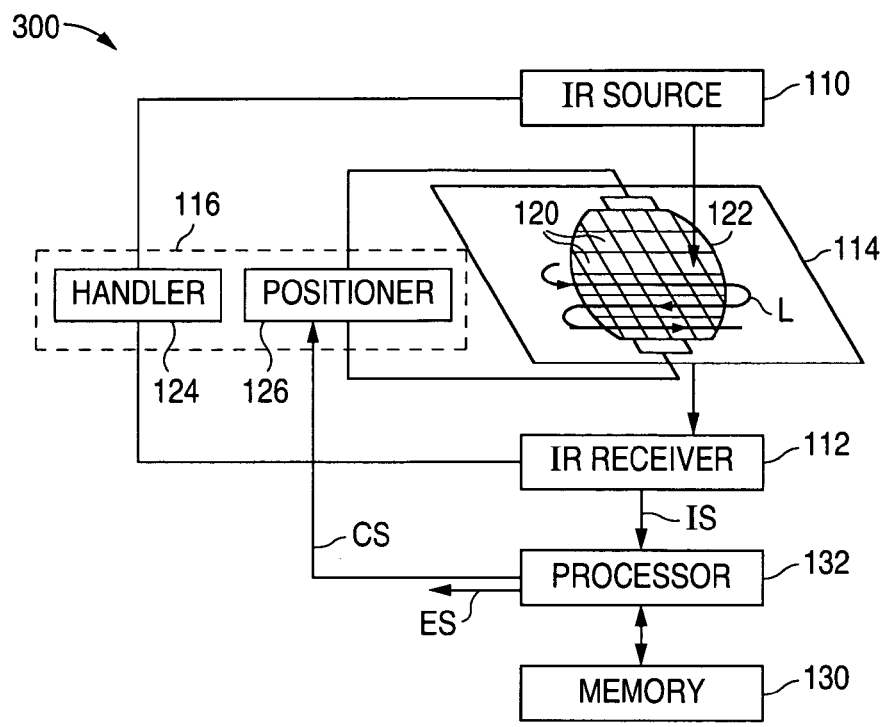
FIG. 3 is a block diagram illustrates an example of a backside defect detector 300 in accordance with an alternate embodiment of the present invention.

FIG. 3 shows a block diagram that illustrates an example of a backside defect detector 300 in accordance with an alternate embodiment of the present invention. Backside defect detector 300 is similar to backside detector 100 and, as a result, utilizes the same reference numerals to designate the structures which are common to both detectors.

As shown in FIG. 3, backside defect detector 300 differs from backside defect detector 100 in that handler 124 of scanner 116 holds IR source 110 and IR receiver 112 in a fixed position, while semiconductor wafer 122 is held and moved about by positioner 126 within plane 114 under the control of processor 132 so that a detected intensity value can be generated for each grid area 120.

In the FIG. 3 embodiment, processor 132 outputs the control signal CS to scanner 116 that controls the movement of positioner 126 and, therefore, the movement of semiconductor wafer 122 so that IR source 110 and IR receiver 112 can be placed on opposite sides of each grid area 120 of semiconductor wafer 122.

Figure 4:
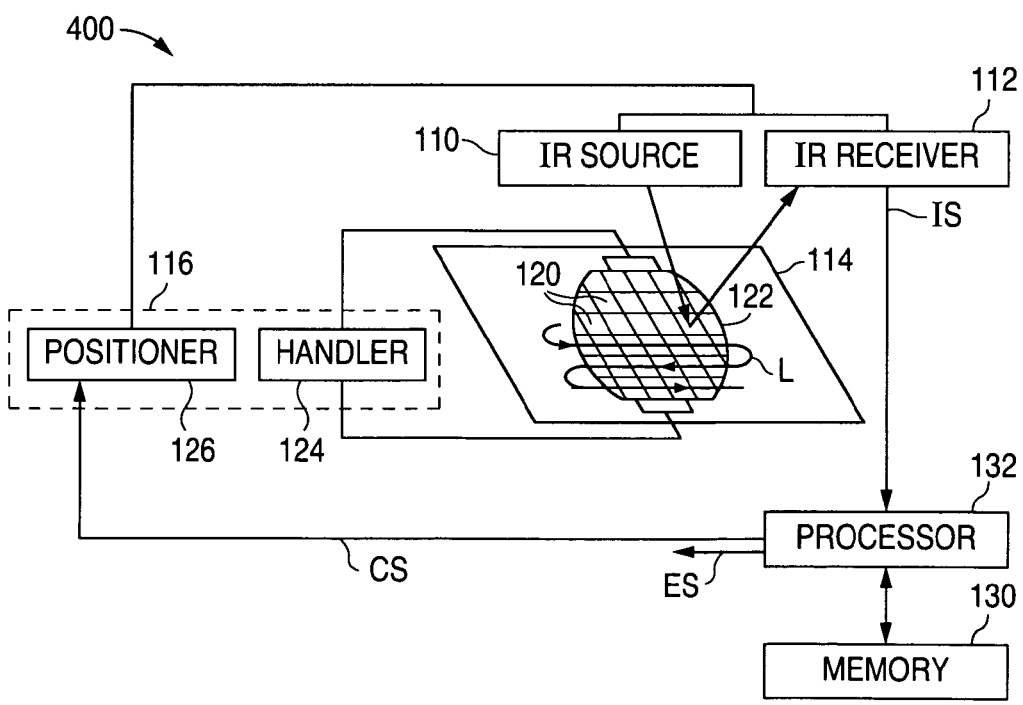
FIG. 4 is a block diagram illustrates an example of a backside defect detector 400 in accordance with an alternate embodiment of the present invention.

FIG. 4 shows a block diagram that illustrates an example of a backside defect detector 400 in accordance with an alternate embodiment of the present invention. Backside defect detector 400 is similar to backside detector 100 and, as a result, utilizes the same reference numerals to designate the structures which are common to both detectors.

As shown in FIG. 4, backside defect detector 400 differs from backside defect detector 100 in that IR source 110 and IR receiver 112 are placed on the same side of plane 114. In this embodiment, when semiconductor wafer 122 is scanned within plane 114, receiver 112 detects the IR light that reflects back from semiconductor wafer 122 rather than IR light that passes through semiconductor wafer 122.

For example, if semiconductor wafer 122 is processed in accordance with the present invention after the gate oxide formation step has been completed, some of the IR light reflects off of the backside of semiconductor wafer 122, some of the IR light passes through wafer 122, some of the IR light reflects off of the top surface of wafer 122, and some of the IR light reflects off of the isolation material and gate oxide regions that contact the top surface of wafer 122.

In addition, in the FIG. 4 embodiment, IR light will also reflect off of any minute oxide regions that have been left on the backside of semiconductor wafer 122 after the gate oxide formation step has been completed. The IR light reflected from any minute oxide regions left on the backside of semiconductor wafer 122 has a greater intensity than any of the other sources of reflected IR light. In the FIG. 4 embodiment, scanner 116 is implemented as shown in the FIG. 1 embodiment, but can alternately be implemented as shown in the FIG. 3 embodiment.

One advantage of backside defect detector 400 over backside defect detector 100 is that backside defect detector 400 can be used during the fabrication of the interconnect structure. As noted above, once the first layer of dielectric material and the contact structures formed through the first layer of dielectric material have been formed, no IR light can pass through semiconductor wafer 122.

However, since backside defect detector 400 detects the presence of unwanted materials on the backside of wafer 122 using reflected IR light, the presence of isolation materials and metals can be detected on the backside side of wafer 122 even though no IR light can pass through wafer 122. In the FIG. 4 embodiment, the IR light reflected off the isolation materials and metals undesirably left on the backside of wafer 122 has a larger intensity that the IR light reflected off of any other surface, material, or, metal.

Thus, the semiconductor wafer can be processed by backside defect detector 400 after the deposition and selective removal of each type of semiconductor material, including metal, that reflects IR light. As a result, the present invention provides a metrology tool that allows a process engineer to determine whether the backside of a semiconductor wafer is clean and flat before proceeding, thereby ensuring that the next lithographic step is more accurate.

It should be understood that the above descriptions are examples of the present invention, and that various alternatives of the invention described herein may be employed in practicing the invention. For example, the IR source can illuminate the entire semiconductor wafer so that only the IR receiver need be moved to perform a scan of the semiconductor wafer. In addition, a semiconductor wafer can be processed by using a combination of backside defect detectors 100, 300, and 400. Thus, it is intended that the following claims define the scope of the invention and that structures and methods within the scope of these claims and their equivalents be covered thereby.

What is claimed is:

1. A backside defect detector comprising:
   an IR receiver to detect an IR light beam at a plurality of locations on a semiconductor wafer, and measure an intensity of the IR light beam to generate a measured intensity for each of the plurality of locations;
   a memory to hold a plurality of stored intensities so that a stored intensity is held for each of the plurality of locations; and
   a controller connected to the IR receiver and the memory, the controller to determine a difference between the measured intensity and the stored intensity for each of the plurality of locations, determine if the difference at any location exceeds an error tolerance, indicate that a material permanently connected to a top side of the semiconductor wafer has been completely removed from a bottom side of the semiconductor wafer when the difference at all locations is below the error tolerance, and indicate that the material remains on the bottom side of the semiconductor wafer when the difference at any location exceeds the error tolerance.

2. The backside defect detector of claim 1 wherein the stored intensity held for a location represents an intensity value of a known good wafer at a corresponding location.

3. The backside defect detector of claim 1 wherein the memory holds a number of stored intensities associated with an end of a corresponding number of etches for each of the plurality of locations, each of the number of stored intensities held for a location representing an intensity value of a known good wafer at a corresponding location following an etch.

4. The backside defect detector of claim 1 wherein the IR light beam measured by the IR receiver to generate the measured intensity is a reflected IR light beam, the reflected IR light beam being reflected off of a single exterior surface of the semiconductor wafer.

5. The backside defect detector of claim 4 wherein the single exterior surface of the semiconductor wafer is the bottom side of the semiconductor wafer.

6. The backside defect detector of claim 1 wherein the material is directly connected to the top side of the semiconductor wafer.

7. The backside defect detector of claim 6 and further comprising:
   an infra-red (IR) source connected to the controller, the IR source to output the IR light beam; and
   a beam director connected to the controller, the beam director to direct the IR light beam to the semiconductor wafer.

8. The backside defect detector of claim 7 wherein the beam director includes a wafer holder, the wafer holder, the IR source, and the IR receiver being positioned so that the IR light beam measured by the IR receiver to generate the measured intensity enters a first exterior side of the semiconductor wafer, passes from the first exterior side completely through the semiconductor wafer to a second exterior side of the semiconductor wafer that lies opposite to the first exterior side, and exits the second exterior side.

9. The backside defect detector of claim 8 wherein the wafer holder lies in a fixed position, and the controller controls a movement of the IR source and the IR receiver so that the IR receiver can receive the IR light beam at each of the plurality of locations.

10. The backside defect detector of claim 8 wherein the IR receiver lies in a fixed position, and the controller controls a movement of the wafer holder so that the IR receiver can receive the IR light beam at each of the plurality of locations.

11. The backside detect detector of claim 8 wherein the wafer holder lies in a fixed position, and the controller controls a movement of the IR receiver so that the IR receiver can receive the IR light beam at each of the plurality of locations.

12. The backside defect detector of claim 1 wherein the IR light beam measured by the IR receiver to generate the measured intensity enters a first exterior side of the semiconductor wafer, passes from the first exterior side completely through the semiconductor wafer to a second exterior side of the semiconductor wafer that lies opposite to the first exterior side, and exits the second exterior side.

13. The backside defect detector of claim 7 wherein the beam director includes a wafer holder, the wafer holder, the IR source, and the IR receiver being positioned so that the IR light beam measured by the IR receiver to generate the measured intensity is a reflected IR light beam, the reflected IR light beam being reflected off of a single exterior surface of the semiconductor wafer.

14. The backside defect detector of claim 13 wherein the IR receiver lies in a fixed position, and the controller controls a movement of the wafer holder so that the IR receiver can receive the IR light beam at each of the plurality of locations.

15. The backside defect detector of claim 13 wherein the wafer holder lies in a fixed position, and the controller controls a movement of the IR source and IR receiver so that the IR receiver can receive the IR light beam at each of the plurality of locations.

16. The backside defect detector of claim 13 wherein the wafer holder lies in a fixed position, and the controller controls a movement of the IR receiver so that the IR receiver can receive the IR light beam at each of the plurality of locations.

17. A method of operating a backside detector, the method comprising:

detecting an IR light beam at a plurality of locations on a semiconductor wafer, and measuring an intensity of the IR light beam to generate a measured intensity for each of the plurality of locations;

holding a plurality of stored intensities so that a stored intensity is held for each of the plurality of locations; determining a difference between the measured intensity and the stored intensity for each of the plurality of locations;

determining if the difference at any location exceeds an error tolerance; indicating that a material permanently connected to a top side of the semiconductor wafer has been completely removed from a bottom side of the semiconductor wafer when the difference at all locations is below the error tolerance; and indicating that the material remains on the bottom side of the semiconductor wafer when the difference at any location exceeds the error tolerance.

18. The method of claim 17 wherein the material is directly connected to the top side of the semiconductor wafer.

19. The method of claim 17 wherein the stored intensity held for a location represents an intensity value of a known good wafer at a corresponding location.

20. The method of claim 17 wherein a number of stored intensities associated with an end of a corresponding number of etches are held for each of the plurality of locations, each of the number of stored intensities held for a location representing an intensity value of a known good wafer at a corresponding location following an etch.

* * * * *

UNITED STATES PATENT AND TRADEMARK OFFICE
CERTIFICATE OF CORRECTION

| | | |
|---|---|---|
| PATENT NO. | : 7,754,502 B1 | Page 1 of 1 |
| APPLICATION NO. | : 11/588742 | |
| DATED | : July 13, 2010 | |
| INVENTOR(S) | : Visvamohan Yegnashankaran | |

It is certified that error appears in the above-identified patent and that said Letters Patent is hereby corrected as shown below:

Title Page,
Item (56) References Cited, OTHER PUBLICATIONS, Page 1, Col. 2, delete "Nanomatrics Incorporated - Process Control Metrology Solutions, [online], [retrieved on Jun. 16, 2006]. Retrieved from the Internet: http://www.nanometrics.com/products/tech_extrem_darkfield.html, pp. 1 of 1."

and replace with

--Nanometrics Incorporated - Process Control Metrology Solutions, [online], [retrieved on Jun. 16, 2006]. Retrieved from the Internet: http://www.nanometrics.com/products/tech_extreme_darkfield.html, pp. 1 of 1.--

Signed and Sealed this

Seventh Day of September, 2010

David J. Kappos
*Director of the United States Patent and Trademark Office*